United States Patent [19]
Löffler

[11] Patent Number: 5,924,974
[45] Date of Patent: Jul. 20, 1999

[54] ELONGATED RADIOACTIVE ELEMENT TO BE ATTACHED TO AN END OF AN ELONGATED WIRE-SHAPED ELEMENT

[75] Inventor: Edgar G. Löffler, Kleve, Germany

[73] Assignee: B.V. Optische Industrie "De Oude Delft", Netherlands

[21] Appl. No.: 08/849,302

[22] PCT Filed: Dec. 23, 1996

[86] PCT No.: PCT/EP96/05889

§ 371 Date: Oct. 3, 1997

§ 102(e) Date: Oct. 3, 1997

[87] PCT Pub. No.: WO97/25103

PCT Pub. Date: Jul. 17, 1997

[30] Foreign Application Priority Data

Jan. 8, 1996 [NL] Netherlands ............ 1002044
Jul. 8, 1996 [NL] Netherlands ............ 1003541

[51] Int. Cl.⁶ ............................................. A61N 5/00
[52] U.S. Cl. ..................................................... 600/3
[58] Field of Search ................................... 600/1–8

[56] References Cited

FOREIGN PATENT DOCUMENTS 9507732  3/1995  WIPO .

*Primary Examiner*—John P. Lacyk
*Attorney, Agent, or Firm*—Louis E. Marn

[57] ABSTRACT

An elongated radioactive element to be fastened to one end of an elongated wire-shaped element, and provided with a front retaining part, a connecting part, and a rear retaining part, as well as segment-shaped elements which are radioactive or are to be made radioactive, which are provided with a center bore and which, enclosed between the front and rear retaining parts, are placed, one behind the other, by means of the center bore over the connecting part and can tilt with respect to each other, all in such a manner that the radioactive element is an elongated member which is supple and flexible over the greatest part of its length, coupling means being provided for connecting the radioactive element to the elongated wire-shaped element.

13 Claims, 2 Drawing Sheets

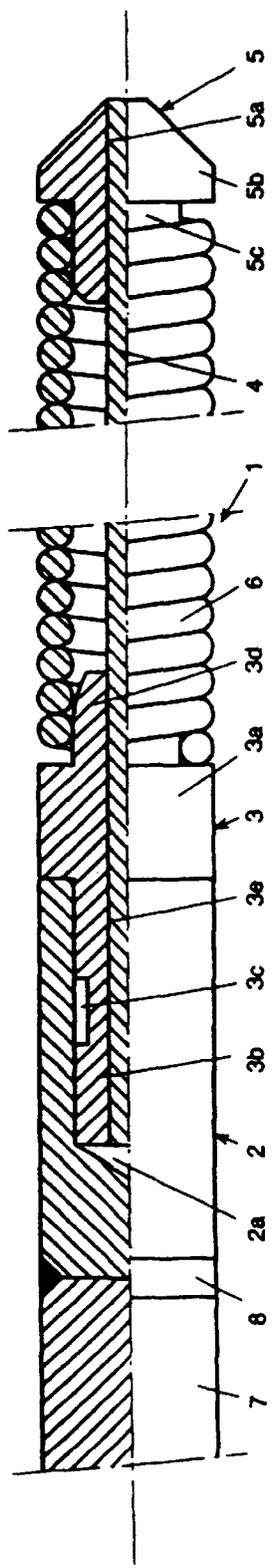
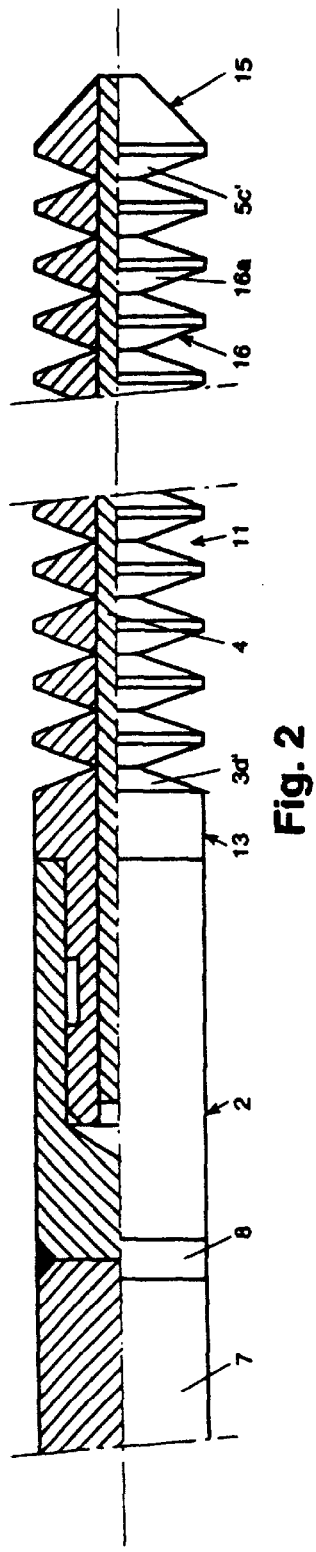
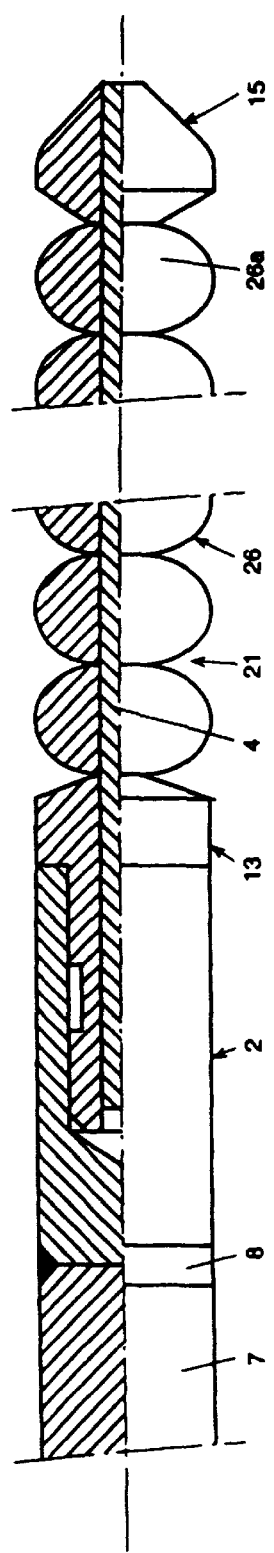

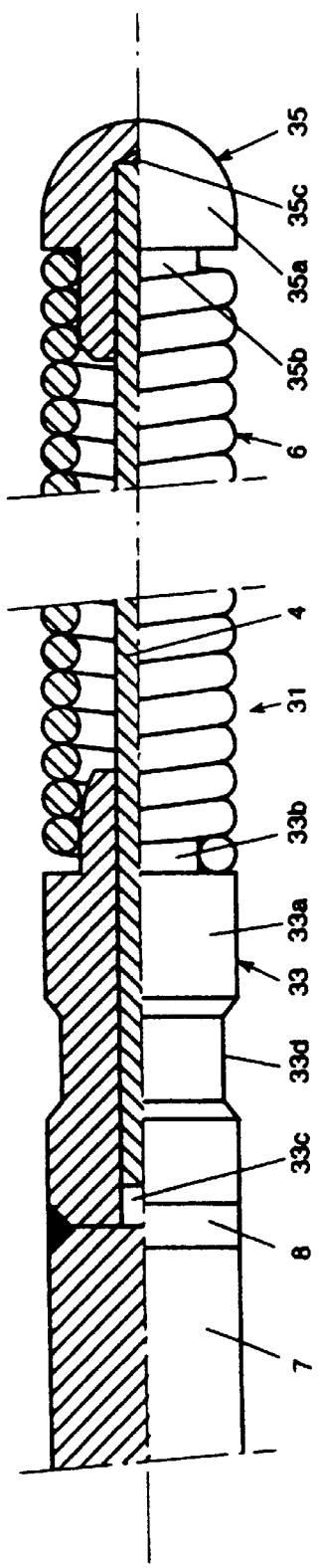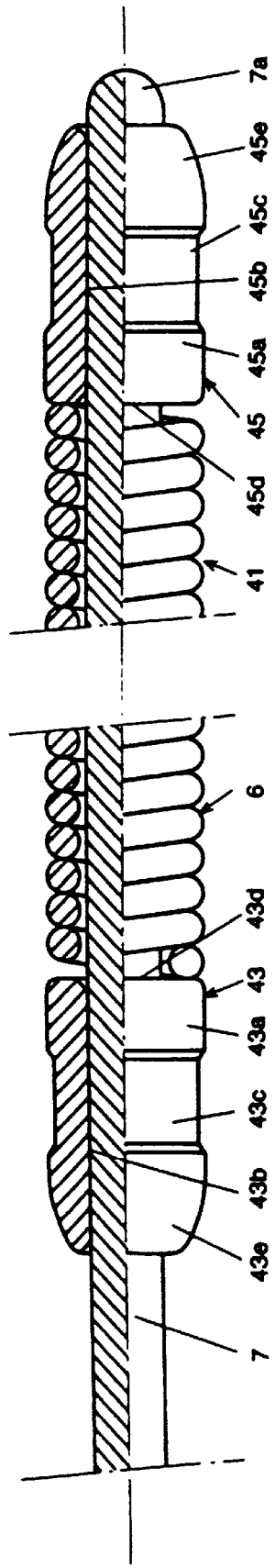

ELONGATED RADIOACTIVE ELEMENT TO BE ATTACHED TO AN END OF AN ELONGATED WIRE-SHAPED ELEMENT

BACKGROUND OF THE INVENTION

1. Field of the Invention

The invention relates to an elongated radioactive element to be attached to an end of an elongated wire-shaped element.

2. Description of the Prior Art

One application of such a radioactive element is its use in the event that local irradiation is desired, particularly, if the place of irradiation is not directly or readily accessible, for instance in the event of a tumor present in a body. In such cases, hollow needles for instance in the case of a mammary tumor, or hollow catheters for instance in the case of a uterine tumor are used within which the radioactive element can be pushed into the desired position for radiation treatment. In order to protect the persons performing the treatment from ionizing radiation, the radioactive element is contained in a shielding housing which is connected by a tube to a needle or catheter. The radioactive element is attached to an end of a wire-shaped element so that the radioactive element can be brought, by remote control, out of the shielding housing through the tube into the desired position for irradiation by the displacement of the wire-shaped element by a drive unit.

Another use also known as intravascular brachytherapy of such a radioactive element is use in the treatment against restenosis by neo-intima proliferation of a blood vessel after a recanalization treatment. Such a treatment of blood vessels around the heart is known, inter alia, as percutaneous transluminal coronary angioplasty (PTCA; in the case of blood vessels around the heart), and atherectomy. Upon such a treatment, a substantially occluded blood vessel (for instance as a result of the deposition of so-called plaque in the lumen of the blood vessel) is stretched by means of an expandable element such as a fluid-inflatable balloon (angioplasty balloon), fastened to an elongated element such as a catheter, in order to permit the blood to flow again substantially unimpeded through the stretched blood vessel. In certain cases, a so called "stent" (metal wire stretcher) is inserted in order, among other things, to prevent "elastic recoil".

In a large number of cases, a new recanalization treatment is found necessary after a relatively short period of time since a constriction again forms in the blood vessel or has already formed. The constriction may be a result of tissue (known as neo-intima hyperplasia or neo-intima proliferation) developing at the stretched place, probably because the wall of the blood vessel was damaged by the stretching. There are strong indications that this formation of tissue can be avoided or at least reduced to a great extent if, during or shortly after the recanalization treatment, the blood-vessel tissue concerned is irradiated with ionizing radiation, in particular β and/or γ radiation, so that a subsequent recanalization treatment is no longer necessary, or in any event a much longer period of time elapses before such a treatment is necessary.

In medical applications of radioactive sources for providing the ionizing radiation mentioned above, radioactive materials are used with half-lives suitable for medical applications. Depending on the application, this half-life is at least a few days. Moreover, for use in intravascular brachytherapy the radiation used should have an average energy $E_{mean}$ of at least 0.6 MeV. $E_{mean}$ is also referred to in the following as β-energy. To this day, choosing a suitable radioactive material meant browsing through voluminous books with extensive tables indicating for each element of the periodical system, whether it is radioactive or not, and if so, in what ways the radioactive element may decay. Thus all radioactive elements whose decay consists of β-decay with an $E_{mean}$ larger than 0.6 MeV and a half-life greater than a few days qualify. In addition to these criteria, other criteria also play a role, e.g., scarcity of the starting material, the toxicity thereof, its mechanical processibility, etc.

In practice, therefore, there is a great need for a source of radioactive material with a β-energy and a half-life that can be employed for vascular brachytherapy without difficulty, and that is inexpensive and easy to process mechanically.

A preferred radioactive source comprises a starting material that after activation produces a radioactive material that decays with nonclinically relevant radioactive decay to a decay product that in turn decays with clinically relevant β-decay. In this way, a "combination source" is provided that is very suitable as β-emitter in intravascular brachytherapy.

In this way, a much greater freedom of choice is obtained with regard to the starting material to be activated, particularly in terms of its cost price, mechanical processibility, toxicity, activability, etc.

The starting material, enriched or not, is activated in a reactor through neutron irradiation. By enriched starting material is understood an isotopic ratio that is changed in favor of one isotope, when compared to the isotopic ratio present in the natural starting material.

In an advantageous manner, the half-life of the activated starting material for a radioactive source is considerably greater than the half-life of the decay product.

More specifically, the half-life of the activated material can exceed 50 hours, while the half-life of the decay product then is less than 10 days. The half-life of the activated material is preferably at least ten times as great as the half-life of the decay product. In this way, a balance is reached relatively quickly between the production and the decay of the decay product. It is known, per se, that such a balance is reached only after about four times the half-life of the decay product. The half-life of the decay product should therefore preferably be less than ten days.

Tungsten is a particularly suited starting material. Natural tungsten consists of two stable isotopes W-184 and W-186. W-186 can be activated through neutron irradiation to W-188 through double neutron capture. In a reactor with sufficient high neutron flux, the double neutron capture should occur with sufficient frequency so as to generate a sufficiently high activity for this application (intravascular brachytherapy).

It should be noted that on account of its 69.4 day half-life, W-188 in principle would qualify as a radioactive source. However, as can be seen from the known tables, the β-energy of the β-radiation emitted by W-188 is much too low, i.e. 0.1 MeV, for it to be considered a likely candidate. Until now, W-188, being difficult to obtain (double neutron capture), was therefore dismissed as a radioactive source. Furthermore, as appears from the same tables, a radioactive material such as Re-188 qualifying in principle because of its β-energy, is not applicable in practice, since its 17-hour half-life is much too short for the present application. And there are still many examples of radioactive materials that satisfy one but not the other criterium.

An especially advantageous radioactive source has tungsten, enriched or not, as a starting material which after activation produces W-188, with the decay product being Re-188.

In this way, a radioactive source is realized, in which Re-188 (which emits the clinically relevant β-radiation) is not produced in advance in a reactor, but is produced rather on-site and continuously through the disintegration of W-188. With regard to the short 17-hour half-life of Re-188, the disintegration time of W-188 to Re-188 is so long (69.4 days) that a continuous production of Re-188 takes place and that apparently a Re-188 source is present with a half-life of more than 69 days, instead of only 17 hours. In this way, therefore, a source is obtained that satisfies both requirements of sufficiently high β-energy and sufficient long half-life. Also a source is obtained of a material, tungsten, having excellent mechanical properties and being very well known through its use as filaments in incandescent lamps.

Specifically, application of a source can take place as a radioactive element that is to be attached to one extremity of an elongated wire-shaped element.

Applying a radioactive element attached to the extremity of an elongated wire-shaped element is known per se from European Patent Application EP-A-0433011.

In order to bring the radioactive element to the stretched place, it must be pushed, at least in part, through a catheter in a blood vessel. In particular, the short turns in the blood vessels of the coronary artery around the heart make a certain flexibility of the element necessary. In order to permit this displacement through a catheter in a blood vessel also to take place flexibly, the radioactive element, which may have the length of a few centimeters, must be sufficiently flexible and pliable in order to be able to slide without problems through the turns of a blood vessel.

OBJECTS OF THE INVENTION

The object of the invention is to design the radioactive element in such a manner that it can adapt itself flexibly to a winding path which is to be followed while nevertheless retaining sufficient stiffness to be able to function, without any particular problem, as front-running part of the moving elongated wire-shaped element.

Another object of the invention is to design such an element in such a manner that radioactive material can be brought as close as possible to the place to be irradiated so that a minimum amount of the radiation emitted by the source is lost by absorption between the source and the place to be irradiated. Furthermore, it is an object here to keep as small as possible the average distance which the ionizing (β and/or γ) radiation is to pass through the radioactive material itself before that material is left.

Still another object of the invention is to be able to manufacture the radioactive element in a relatively simple manner, that is to say, the manufacture and activation of the element separate from the elongated wire-shaped element.

SUMMARY OF THE INVENTION

For this purpose, according to the invention, it is proposed that the radioactive element be formed of a front retaining part, a connecting part, and a rear retaining part, as well as segment-shaped elements which are or are to be made radioactive, which are provided with a center bore, and which, contained between the front and the rear retaining part, are placed, one behind the other, by means of the center bore over the connecting part and can tilt with respect to each other, all in such a manner that the radioactive element is an elongated member which is supple and flexible over the greatest part of its length, coupling means being provided for connecting the radioactive element to the elongated wire-shaped element. As a result of these measures, by the forming of the member from segment shaped elements which are tiltable with respect to each other an extremely supple and flexible unit can be obtained which is readily able to follow the turns in, for instance, a blood vessel, in which connection, the coherence in longitudinal direction of the element is assured by the holding together between the front and rear retaining parts by the connecting part of the radioactive material, which in order to be supple and flexible does not have to be able in fact to stretch in longitudinal direction. Due to the fact that the radioactive material is arranged around the connecting part, the further advantage is obtained that the radioactive material is concentrated as far as possible on the outside of the elongated radioactive element and in this way is positioned as close as possible to the place to be irradiated, whereby a minimum amount of ionizing radiation is lost by absorption in the radioactive material itself or between the source and the place to be irradiated.

In accordance with a further embodiment of the invention, it is preferred that each segment-shaped part have the shape of a helically bent wire part and that all segment-shaped parts are part of or are connected together to form an elongated supple, flexible member having the shape of a coil spring. An element designed in this way can be produced relatively simply and is, inherently, supple and flexible, in which connection, an undesired kinking of such a coil-shaped element is effectively prevented by enclosing it on the connecting part, between the front and the rear retaining parts. If, in the case of such an embodiment the connecting part is a wire having such a diameter that the coil-spring shaped member surrounds the wire with relatively large clearance, it is furthermore preferable that both the retaining parts be provided with centering collars which face each other and have an outside diameter which is substantially equal to the diameter of the center bore in the coil-spring shaped member. If the connecting part consists of a wire which connects the two retaining parts and forms the extension of the elongated wire-shaped element and receives the coil-spring-shaped member with slight clearance, it is preferred that the retaining parts be sleeve parts which can be clamped onto the elongated wire-shaped element.

In accordance with another embodiment of the invention, it can be provided that each segment-shaped part is formed as a bead provided with a central threading hole, having a cross section which decreases in the direction away from the hole. In this connection, bead can have a round, and in particular an elliptical or circular, cross section, while it is also possible for each bead to be designed as a torus shaped body of revolution with a substantially trapezoidal cross-sectional profile. The beads can in this connection be strung as a chain on a wire acting as connecting part and thus sit enclosed between a front and a rear retaining part, which parts are designed as sleeve parts which can be clamped on the wire. In the event that the connecting part is not the extension of the elongated wire-shaped element, the rear retaining part may be provided with coupling means for connection to the elongated wire-shaped element. The coupling means may consist of an end plane having a surface equal to the cross section of the elongated wire-shaped element, with the rear retaining part and the elongated wire-shaped element being connected to each other by welding, soldering, gluing or otherwise, or else of a part which narrows down in step shape and is to be fastened in a bore arranged in a coupling element which has an outside diameter equal to that of the elongated wire-shaped element and is connectable by welding, soldering, gluing or the like with the elongated wire-shaped gluing or the like with the elongated wire-shaped element. Upon the use of such a connection, the elongated radioactive element may be produced entirely separate from the elongated wire-shaped element. This has the extra advantage that this element can be made in a suitable manner, whereupon it is activated and then connected with the elongated wire-shaped element.

BRIEF DESCRIPTION OF THE DRAWINGS

Referring to embodiments shown in the drawing, the elongated radioactive element according to the invention will now be discussed in further detail. In the drawing:

FIG. 1 shows a first embodiment of the elongated radioactive element according to the invention, which element is fastened to a wire-shaped element and is shown half in cross section and half in elevation; and FIGS. 2, 3, 4 and 5 show a second, third, fourth and fifth embodiment of the elongated radioactive element according to said application of a source according to the invention, shown in a manner similar to that of FIG. 1.

DETAILED DESCRIPTION OF THE DRAWINGS

The elongated radioactive element 1 shown in FIG. 1 is formed of a fastening part 2, a rear retaining part 3, a connecting part 4, a front retaining part 5, and a radioactive part 6. The radioactive element 1 is fastened at its end face to an elongated wire-shaped element 7 which is made of a supple, flexible cable, only one end of which is shown. The attachment is effected by means of a welded or soldered connection 8, in which connection, in order to obtain a smooth continuous unit, the fastening part 2 consists of a cylindrical element having the same diameter as the wire-shaped element 7.

The fastening part 2 is provided with a blind lengthwise bore 2a which extends opposite from the end face connected to the wire-shaped element 7. The rear retaining part 3 is provided with a cylindrical middle part 3a having the same diameter as the fastening part 2. Adjoining this middle part 3a to the left in the drawing there is a cylindrical part 3b which has a diameter which fits in the blind lengthwise bore 2a. The cylindrical part 3a can be fastened by a suitable method in the lengthwise bore 2a. This may be done by welding, soldering, gluing or the like, but other methods of attachment such as clamping and threading also enter into consideration. In the part 3a, there is a circumferential recess 3c. Adjoining the middle part 3a on the right in the drawing, there is a fastening pin 3d having a diameter which is smaller than that of said middle part 3a. Furthermore, the middle part is provided with a longitudinal central through bore 3e which has such a diameter that the connecting part 4 which consists of a wire can be inserted through it with a close fit. The connecting part 4 can be clamped in the longitudinal central through bore 3e by, for example, deforming the cylindrical part 3b at the place of the circumferential recess 3c. Of course, any other suitable method of attachment can also be used, such as welding, soldering, gluing or the like. The circumferential recess 3c can also be used for the application of glue.

The end of the connecting part 4 located opposite the end fastened in the longitudinal central through bore 3e is inserted with a close fit in a longitudinal bore 5a in the front retaining part S, which is provided with a truncated conical head 5b and a fastening pin 5c adjoining same to the left in the drawing and having a diameter equal to that of the fastening pin 3d. The connecting part 4 is fastened in the longitudinal bore 5a of the front retaining part 5 by some suitable method, for instance, welding, soldering, gluing or the like.

Between the front retaining part 5 and the rear retaining part 3 there is enclosed the radioactive part 6 which has the shape of a coil spring with an outside diameter substantially equal to that of the cylindrical middle part 3a and the truncated conical head 5b and an inside diameter substantially equal to that of the fastening pins 3d and 5c.

In this way, there is obtained an extremely supple and flexible radioactive element 1 which forms the front end of an elongated wire, all in such a manner that said radioactive element 1 can bend in the same manner as the wire in order to follow a curve in a guide path, since the connecting part 4 and the radioactive part 6 behave in the same manner as a supple, flexible wire. The guide path can consist in this connection of a catheter or similar element which is introduced into the human body and extends, for instance, via a blood vessel up to the place to be treated.

One advantage of the present radioactive element 1 is that the parts forming it can be made before the activation of the radioactive element, whereupon the fastening element is connected with the end of the elongated wire-shaped element 7 and the front retaining part 5, the connecting part 4, the radioactive part 6 and the rear retaining part 3 can be assembled to form a unit, whereupon the radioactive part 6 is activated and finally the cylindrical part 3b is fastened in the lengthwise bore 2a. Thus, the element is manufactured with a minimum risk of exposure to radiation.

The radioactive element 11 shown in FIG. 2 is provided with the same fastening part 2 as shown in FIG. 1. The fastening part 2 is fastened by means of a weld or solder connection 8 at the end face to the end of an elongated wire-shaped element 7. The radioactive element 11 is furthermore provided with a rear retaining part 13 which is similar to the part 3 in FIG. 1, except that the fastening pin 3d is replaced by a truncated conical part 3d'. There is also again present a connecting part 4 which is fastened in the rear retaining part 3 and the front retaining part 15, which is substantially identical to the rear retaining part S in FIG. 1, in this case also the fastening pin 5c being replaced by a truncated conical part 5c'.

In the embodiment shown in FIG. 2 the radioactive part 16 is composed of a number of disk-shaped elements 16a, all of which are provided with a center bore and are threaded as beads on the connecting part 4. By this embodiment of the radioactive part 16, the radioactive element 11 is imparted the desired suppleness and flexibility, that is to say, it can take curves in a guide path in the same manner as the wire-shaped element 7 without any problem. The production, assembling and activating of the radioactive element 11 can be effected in the same advantageous manner as in the case of the radioactive element 1 of FIG. 1.

The radioactive element 21 shown in FIG. 3 is identical to the radioactive element 11 of FIG. 2 with respect to the fastening part 2, the rear retaining part 13, the connecting part 4, and the front retaining part 15. The radioactive element 21 is also connected with an elongated element 7 by means of a weld or solder connection 8. The embodiment of the radioactive part 26 differs, in the manner that it is composed of bead-like elements 26a, that is to say elements of rotational symmetry having a rounded cross section and a center bore.

FIG. 4 shows a radioactive element 31 which is formed of a rear retaining part 33, a connecting part 4, a front retaining part 35, and a radioactive element 6. Therefore, the front and rear retaining parts are different from the embodiment according to FIG. 1. The most important difference is the absence of a fastening part, the task of which is taken over by the rear retaining part 33, which is provided for this purpose with a cylindrical part 33a which has the same outside diameter as the elongated element 7 and the one end of which is fastened directly at its end surface by a weld or solder connection 8 to the elongated element 7. The other end of the cylindrical part 33a bears a fastening pin 33b which is similar to the fastening pin 3d of FIG. 1. As in the previous embodiment, the connecting part 4 is to fastened in a longitudinal bore 33c. This can be done, for instance, by clamping at the place of a circumferential recess 33d in the cylindrical part 33a. The front retaining part 35 is provided with a semi-spherical head 35a to the left of which in the drawing there is joined a fastening pin 35b, similar to the fastening pin 5c in FIG. 1. Furthermore, the front retaining part 35 is provided with a blind bore 35c to receive the connecting part 4, which must be fastened in the bore. As already stated, this can be done by welding, soldering, gluing or the like. Another possibility is clamping, for which the fastening pin 35 may, for instance, be provided with a circumferential recess.

FIG. 5 shows a radioactive element 41 provided with a radioactive part 6 in the form a coil spring which is enclosed between two identically designed retaining parts the rear one of which is indicated by the reference numeral 43 and the front one by the reference numeral 45. Each retaining part 43, 45 is formed by a sleeve-like body 43a, 45a with central, continuous longitudinal bore 43b, 45b and circumferential recess 43c, 45c. Furthermore, each retaining part 43, 45 is provided with a flat end 43d, 45d and a rounded and beveled end 43e, 45e.

Differing from the preceding embodiments, there is no connecting part in the embodiment shown in FIG. 5. The task of that part is taken over by the elongated element 7 which is provided with a rounded end 7a. The radioactive element 41 is formed by the rear retaining part 43 which is pushed over the elongated element 7, the rounded and beveled end 43a in front and held fast thereon, for instance by clamping at the place of the circumferential recess 43c. Thereupon, the radioactive part 6, or the part 6 which is to be made radioactive, is pushed until it comes against the flat end 43d on the elongated element. Finally, the front retaining part 45 is pushed with the flat end 45d in front until it rests against the part 6 on the elongated element 7 and thereupon held fast, for instance at the place of the circumferential recess 45c. The rear retaining part 43 is in this connection fastened at such a place on the elongated element 7 that the rounded end 7a still protrudes from the front retaining part 45.

The embodiment of FIG. 5 has the advantage of simplicity, both in terms of manufacture and assembly. In fact, only two different parts have to be made, while the attachment is effected by only two simple clamping actions.

It is obvious that, within the scope of the present invention as set forth in the accompanying claims, many modifications and variations are possible in addition to those discussed above and in the five embodiments shown in the drawing. Thus, in the embodiment according to FIG. 4 or FIG. 5, the coil-shaped radioactive part may also be replaced by the disk-shaped elements of FIG. 2 or the bead-shaped elements of FIG. 3. In addition to the methods of fastening the various parts together which have been shown, other suitable known methods of attachment can be used, some of which have already been mentioned.

The source material may be coated with a non- or slightly activatable material such as, for instance, TiN, TiO, Ti, Si, SiO, SiN. The other parts of the radioactive element can for instance be made of titanium or vanadium.

The choice of tungsten (through activation, W-188 with a half-life of 69.4 days is produced, the decay product being Re-188 with a half-life of 17 hours) as a starting material has many advantages:

inexpensive easily obtainable easy to work on easy to activate through a neutron source.

Moreover, tungsten can be applied in a proper way as a starting material in various forms, for instance:

spiral stent (small metal wire stretcher)

(very) thin wire disc- or bead-shaped elements.

The source may be implemented as a stent, as mentioned above; a stent is in direct contact with the wall of the blood vessel, so that a great source strength is unnecessary. A Ti-stent alloyed with W may be used in an advantageous manner. A very thin wire may also be used as a source, especially for small blood vessels. Such a wire should preferably be coated. In small blood vessels, such a thread may come in contact with the walls and only a small source strength is required.

I claim:

1. An elongated, radioactive element for radiotherapy comprising:

a front retaining element, a connecting element, a rear retaining element, radioactive segment-shaped elements having a center bore, positioned on said connecting element between said front and said rear retaining elements, angularly displaceable with respect to adjacent radioactive segment-shaped elements thereby providing a supple and flexible radioactive element;

an elongated wire-shaped element; and coupling means for connecting said radioactive element to said elongated wire-shaped element.

2. The elongated radioactive element according to claim 1, wherein each segment-shaped element has the shape of a helical wire element forming an elongated supple, flexible radioactive member having the shape of a coil spring.

3. The elongated radioactive element according to claim 1, wherein each segment-shaped element is bead-shaped and provided with a threaded center bore, each bead having a decreasing cross section in direction away from said center bore.

4. The elongated radioactive element according to claim 3, wherein each said bead is in cross section.

5. The elongated radioactive element according to claim 3 comprised in that each said bead is the shape of a toroidal body of revolution having a substantially trapezoidal cross-sectional profile.

6. The elongated radioactive element according to claim 1, wherein said connecting element comprises a wire connecting said front retaining element and said rear retaining element.

7. The elongated radioactive element according to claim 6, wherein said wire has a diameter less than, the diameter of said center bore in said segment-shaped elements.

8. The elongated radioactive element according to claim 7, wherein said wire forms an extension of said elongated wire-shaped element and said front and rear retaining elements comprise sleeve elements which can be secured on said elongated wire-shaped element.

9. The elongated radioactive element according to claim 7, wherein said front and rear retaining elements comprise sleeve elements which can be secured on said wire, said rear retaining element being provided with said coupling means for connection to said elongated wire-shaped element.

10. The elongated radioactive element according to claim 9, wherein said coupling means comprises an end plane having a surface equal to the cross section of said elongated wire-shaped element, said rear retaining element and said elongated wire-shaped element adapted to interconnect.

11. The elongated radioactive element according to claim 9, wherein said coupling means comprises a coupling element having an outside diameter equal to that of said elongated wire-shaped element and is secured thereto said coupling element having a bore for receipt of a step-shaped locking element for securing said radioactive element.

12. The elongated radioactive element according to claim 2, wherein said connecting element is a wire having a diameter less than the diameter of said center bore of said segment-shaped members having the shape of said coil spring said front retaining element and said rear retaining element being provided with opposing centering collars having an outside diameter which is substantially equal to the diameter of said center bore in said coil spring-shaped radioactive member.

13. The elongated radioactive element according to claim 3, wherein each said bead is elliptical in cross section.

* * * * *